(12) United States Patent
Senda et al.

(10) Patent No.: US 9,621,822 B2
(45) Date of Patent: Apr. 11, 2017

(54) IMAGING UNIT AND IMAGING METHOD

(71) Applicant: Sony Corporation, Tokyo (JP)

(72) Inventors: Michiru Senda, Kanagawa (JP);
Shinichi Watanabe, Kanagawa (JP);
Daisuke Kawazoe, Tokyo (JP);
Yuichiro Minami, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 14/431,970

(22) PCT Filed: Sep. 27, 2013

(86) PCT No.: PCT/JP2013/076388
§ 371 (c)(1),
(2) Date: Mar. 27, 2015

(87) PCT Pub. No.: WO2014/054546
PCT Pub. Date: Apr. 10, 2014

(65) Prior Publication Data
US 2015/0288890 A1    Oct. 8, 2015

(30) Foreign Application Priority Data

Oct. 4, 2012 (JP) .................. 2012-222393
Nov. 20, 2012 (JP) .................. 2012-254677

(51) Int. Cl.
*H01L 27/146* (2006.01)
*H04N 5/321* (2006.01)
(Continued)

(52) U.S. Cl.
CPC ............. *H04N 5/321* (2013.01); *G01T 1/161* (2013.01); *G01T 1/17* (2013.01); *G01T 1/247* (2013.01);
(Continued)

(58) Field of Classification Search
CPC .................. G01T 1/17; G01T 1/247
See application file for complete search history.

(56) References Cited

U.S. PATENT DOCUMENTS

| 7,659,518 B2* | 2/2010 | Adachi | A61B 6/4233 250/370.09 |
| 2010/0215146 A1* | 8/2010 | Rao | H03M 1/183 378/62 |
| 2012/0320246 A1* | 12/2012 | Ikuma | H04N 5/3575 348/300 |

FOREIGN PATENT DOCUMENTS

| JP | 2002-199292 A | 7/2002 |
| JP | 2009-272673 A | 11/2009 |
| JP | 2010-263483 A | 11/2010 |

* cited by examiner

*Primary Examiner* — Kiho Kim
(74) *Attorney, Agent, or Firm* — Chip Law Group

(57) ABSTRACT

There is included: a light receiving device configured to receive light and convert the received light into a light detection signal; a pixel transistor connected to the light receiving device and configured to control connection between the light receiving device and a signal line; a low-pass filter configured to be applied with respect to the light detection signal; an A-D converter configured to convert an output signal of the low-pass filter into digital data; and a sequencer configured to, prior to causing the A-D converter to operate to output the digital data, control the pixel transistor to be in an ON state and thereby maintain the light receiving device to be connected to the signal line, in a state in which the low-pass filter is caused to function effectively with respect to the light detection signal.

7 Claims, 9 Drawing Sheets

(51) Int. Cl.
*H04N 5/32* (2006.01)
*H04N 5/361* (2011.01)
*H04N 5/374* (2011.01)
*H04N 5/378* (2011.01)
*G01T 1/161* (2006.01)
*G01T 1/24* (2006.01)
*H04N 5/3745* (2011.01)
*G01T 1/17* (2006.01)
*A61B 6/00* (2006.01)

(52) U.S. Cl.
CPC ............... *H04N 5/32* (2013.01); *H04N 5/361* (2013.01); *H04N 5/374* (2013.01); *H04N 5/378* (2013.01); *H04N 5/37455* (2013.01); *A61B 6/4208* (2013.01)

IMAGING UNIT AND IMAGING METHOD

TECHNICAL FIELD

The present disclosure relates to an imaging unit and an imaging method that mainly shoot a fluoroscopic image, etc. of a shooting target with the use of a radiation such as an X-ray or a γ-ray.

BACKGROUND ART

In recent years, a radiation imaging unit that is capable of not only storing a shot image as digital data but also shooting a moving image has been in wide spread use instead of a so-called X-ray imaging unit that uses a film in the medical industry.

The radiation imaging unit uses a radiation called X-ray, for example. It is therefore necessary to reduce an exposure dose of X-ray with respect to a human body to be shot as much as possible. Accordingly, it is desired for an imaging section that detects the X-ray to have high sensitivity with respect to the X-ray and to have a high S/N ratio.

Incidentally, Patent Literature 1 is a prior art literature that discloses a technology that is considered to be similar to the present disclosure.

PRIOR ART LITERATURE

Patent Literature

Patent Literature 1: Japanese Unexamined Patent Application Publication No. 2010-263483

SUMMARY OF THE INVENTION

An imaging section in a radiation imaging unit may be formed of an amorphous silicon TFT (Thin Film Transistor), a low-temperature polysilicon TFT, or the like. In particular, developments have been made employing the low-temperature polysilicon TFT that has an ON resistance value that is lower than an ON resistance value of the amorphous silicon TFT in order to improve various performances such as sensitivity.

However, although the resistance value is lower than that of the amorphous silicon TFT, a thermal noise may disturb improvement in sensitivity. It has been therefore difficult to achieve an imaging section having high sensitivity.

Accordingly, it is desirable to provide an imaging unit including an imaging section that is less influenced by the thermal noise and has high sensitivity, and utilizing a low-dose radiation such as a low-dose X-ray to achieve a practical imaging performance. It is also desirable to provide an imaging method.

A first imaging unit of an embodiment of the present technology includes: a light receiving device configured to receive light and convert the received light into a light detection signal; a pixel transistor connected to the light receiving device and configured to control connection between the light receiving device and a signal line; a low-pass filter configured to be applied with respect to the light detection signal; an A-D converter configured to convert an output signal of the low-pass filter into digital data; and a sequencer.

The sequencer is configured to, prior to causing the A-D converter to operate to output the digital data, control the pixel transistor to be in an ON state and thereby maintain the light receiving device to be connected to the signal line, in a state in which the low-pass filter is caused to function effectively with respect to the light detection signal.

A second imaging unit of an embodiment of the present technology includes: a light receiving device configured to receive light and convert the received light into a light detection signal; a pixel transistor connected to the light receiving device and configured to control connection between the light receiving device and a signal line; a low-pass filter including a capacitor and configured to be applied with respect to the light detection signal; an A-D converter configured to convert an output signal of the low-pass filter into digital data; a sample and hold circuit configured to share the capacitor with the low-pass filter, and connected between the low-pass filter and the A-D converter and; and a sequencer.

The sequencer is configured to control the pixel transistor to be in an ON state in a state in which the low-pass filter is caused to function effectively with respect to the light detection signal, after predetermined time has elapsed thereafter, cause the sample and hold circuit to perform a hold operation while maintaining a state in which the pixel transistor is controlled to be in the ON state, cause the A-D converter to operate to output the digital data, and thereafter, control the pixel transistor to be turned off.

An imaging method of an embodiment of the present technology includes: controlling a pixel transistor to be turned on, the pixel transistor being connected to a light receiving device and being configured to control connection between the light receiving device and a signal line, and the light receiving device being configured to receive light and convert the received light into a light detection signal; causing a low-pass filter to operate with respect to the light detection signal; and after predetermined time has elapsed thereafter, causing a sample and hold circuit to perform a hold operation while maintaining a state in which the pixel transistor is controlled to be in an ON state, the sample and hold circuit being configured to be connected to the low-pass filter.

According to the first and second imaging units and the imaging method of the embodiments of the present technology, the imaging section that is less influenced by the thermal noise and has high sensitivity is provided, and it is possible to utilize a low-dose radiation such as a low-dose X-ray to achieve a practical imaging performance.

A problem, a configuration, and an effect other than those described above are disclosed by the following description of embodiments.

EMBODIMENTS OF THE INVENTION

[General Configuration of Radiation Imaging Unit]

Figure 1:
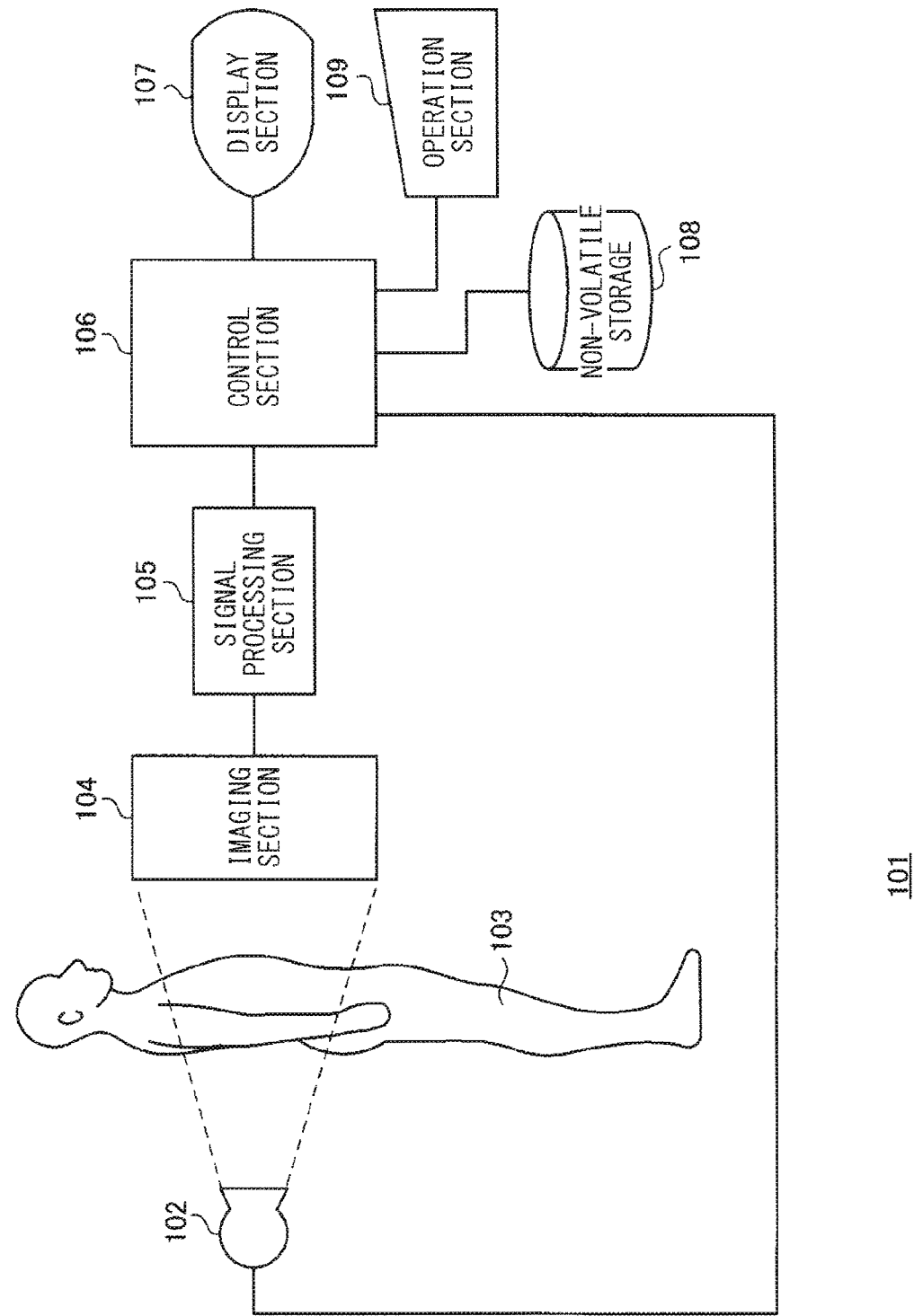
FIG. 1 is a block diagram of a radiation imaging unit related to an embodiment of the present disclosure.

FIG. 1 is a block diagram of a radiation imaging unit related to an embodiment of the present disclosure.

An X-ray radiated from an X-ray tube 102 passes through a subject 103 and is applied to an imaging section 104 in a radiation imaging unit 101. The imaging section 104 produces small electric charge based on the received X-ray.

The signal processing section 105 generates image data based on the electric charge produced by the imaging section 104.

A control section 106 receives the image data from the signal processing section 105, and displays the received image data on a display section 107 and stores the received image data in a non-volatile storage 108.

The control section 106 also receives an operation to an operation section 109, and thereby performs ON-OFF control of the X-ray tube 102.

Out of the components configuring the radiation imaging unit 101, the control section 106 may be configured of a personal computer, for example. The radiation imaging unit 101 may be achievable by causing a processor provided in the personal computer to execute a program of displaying a still image or a moving image to display the image data inputted from the signal processing section 105.

It is to be noted that, instead of performing an image process, the process of storing the image data with the use of the non-volatile storage 108, etc., the image data outputted by the signal processing section 105 may be directly displayed on the display section 107, or the image data outputted by the signal processing section 105 may be stored by a video recorder or the like.

The present technology mainly relates to the signal processing section 105 that is connected to the imaging section 104. It is to be noted that detail description of the control section 106 is omitted.

[Configuration of Imaging Section 104]

Figure 2A:
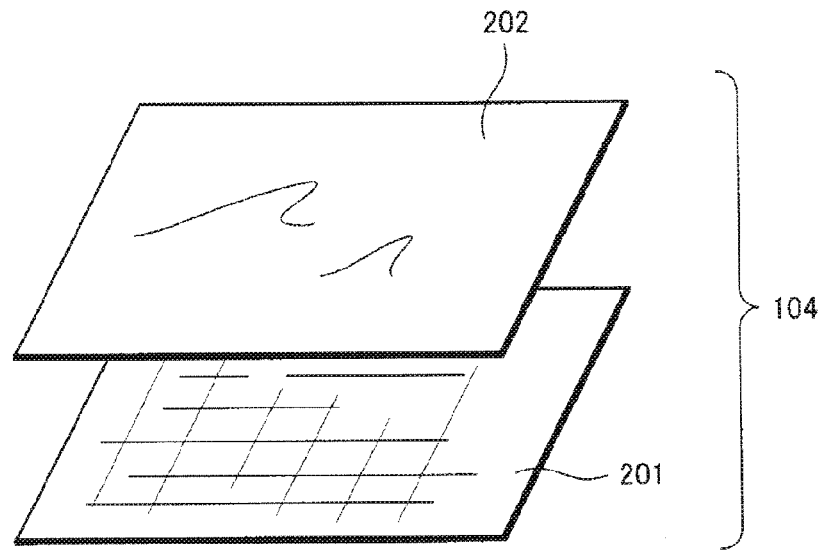
FIG. 2A is an exploded perspective view illustrating an appearance of an imaging section.
Figure 2B:
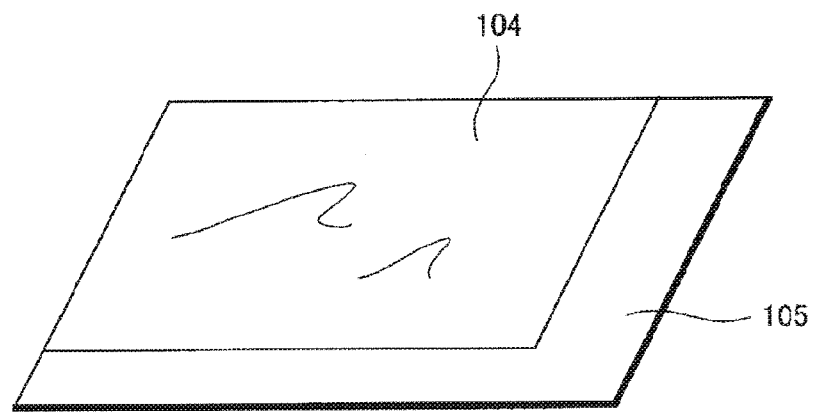
FIG. 2B is a perspective view illustrating the appearance of the imaging section.
Figure 2C:
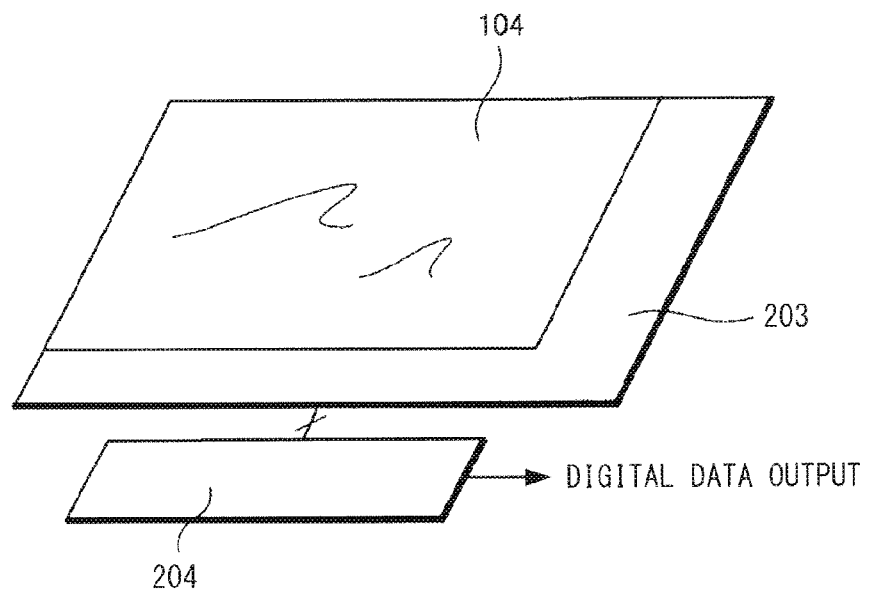
FIG. 2C is a perspective view illustrating the appearance of the imaging section.

FIGS. 2A to 2C are an exploded perspective view and perspective views that illustrate an appearance of the imaging section 104. FIG. 2A is the exploded perspective view of the imaging section 104. The imaging section 104 includes a sensor array 201 and a scintillator 202 that covers an imaging surface of the sensor array 201.

The sensor array 201 may be configured of a low-temperature polysilicon TFT, and may include photodiodes and switching transistors that are provided in a lattice form.

The scintillator 202 may be a fluorescent film that converts the X-ray into visible light. Plastic including anthracene or a sheet in which a fluorescent substance such as sodium iodide, cesium iodide, or gadolinium oxide sulfur (GOS) is applied or enclosed may be employed therefor. Further, in the case where cesium iodide is used, the scintillator 202 may not be formed as a sheet but may be formed by direct deposition on the sensor array.

FIG. 2B is the perspective view of the imaging section 104. A circuit board of the signal processing section 105 is connected to a longitudinal portion and a lateral portion of the sensor array 201 that has the imaging surface attached with the scintillator 202. Electric charge outputted by a photodiode included in the sensor array 201 is extremely small. For this reason, the signal processing section 105 is configured in a form directly connected to the sensor array 201 in order to reduce a wiring length as much as possible.

FIG. 2C is the perspective view illustrating another form of mounting the imaging section 104. The signal processing section 105 is divided into an analog circuit section 203 and a digital circuit section 204. Further, the analog circuit section 203 may be configured by COG (Chip On Glass: a mounting technique of directly providing an LSI on a glass substrate or the like), COF (Chip On Film: a mounting technique of directly providing an LSI on a film substrate made of a material such as polyimide), or the like. The digital circuit section 204 is mounted on a usual circuit board.

Figure 3:
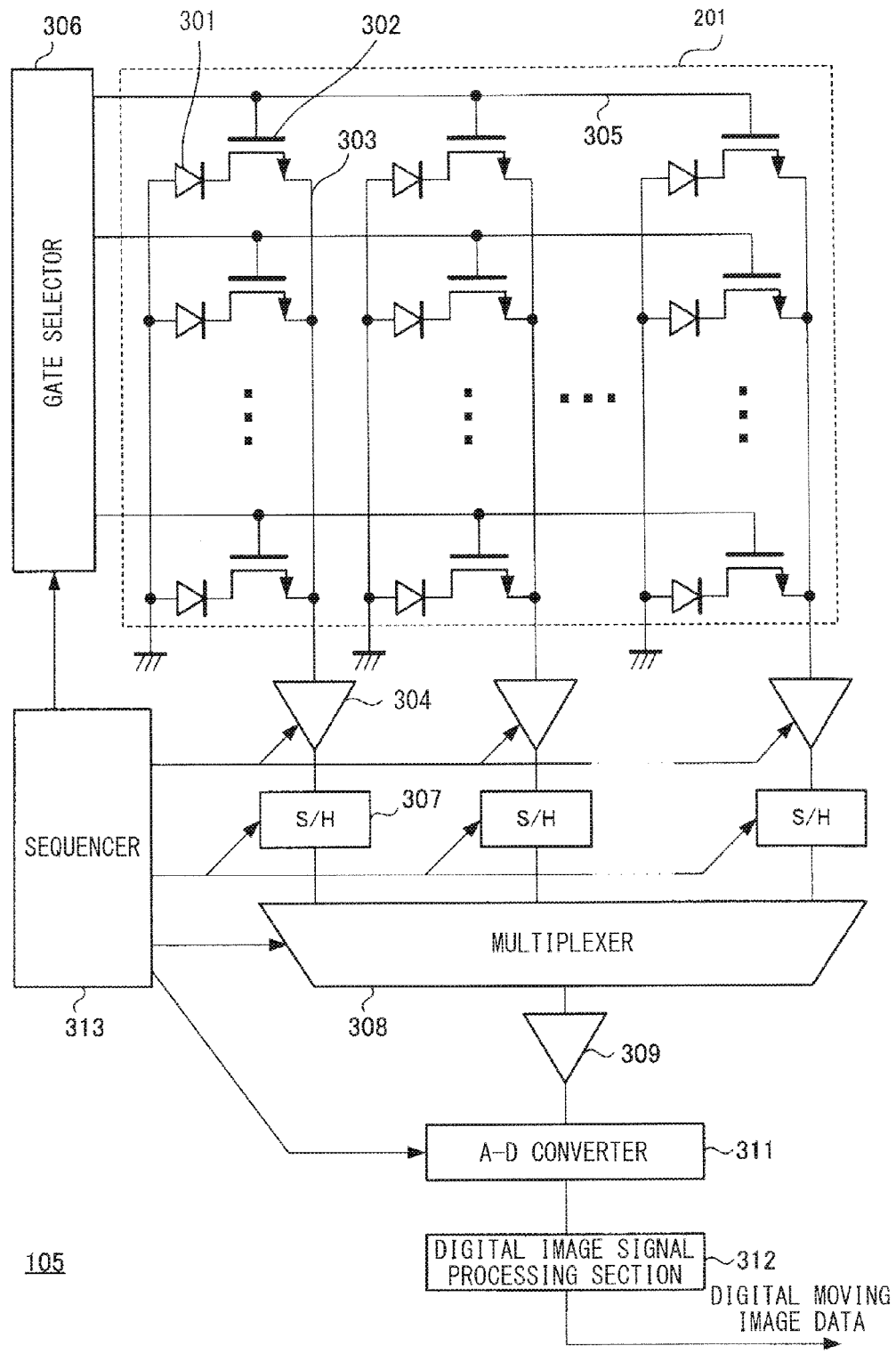
FIG. 3 is a block diagram of a signal processing section that includes a sensor array.

FIG. 3 is a block diagram of the signal processing section 105 provided with the sensor array 201.

As described above, in the sensor array 201, photodiodes 301 and pixel transistors 302 that configure pixels are formed in a mesh-like form. The photodiodes 301 may be each a light receiving device.

The pixel transistors 302 may be each an MOSFET, for example, and may each transmit, to a signal line 303, output electric charge resulting from photoelectric conversion performed by the photodiode 301.

Sources of the pixel transistors 302 in each column are connected to the common signal line 303, and the common signal line 303 is further connected to a charge amplifier 304.

Gates of the pixel transistors 302 in each row are connected to a common control line 305. A gate selector 306 causes one of the plurality of control lines 305 corresponding to "row" to have a high potential, and thereby selects pixels in the corresponding "row".

The charge amplifiers 304 are connected to all of the columns of the pixels configuring the sensor array 201. Further, a sample and hold circuit section 307 is connected immediately downstream of each of the charge amplifiers 304. It is to be noted that the description of the sample and hold circuit is abbreviated as "S/H" in FIG. 3.

Output voltages of the plurality of sample and hold circuit sections 307 are selected by a multiplexer 308, and the selected output voltages are supplied to an amplifier 309. An output voltage of the amplifier 309 is supplied to an A-D converter 311, and is converted into digital data. The amplifier 309 amplifies an output voltage of a CDS 413 that is described later referring to FIG. 4.

The digital data that is outputted by the A-D converter 311 and corresponds to the output voltage of the amplifier 309 is supplied to a digital image signal processing section 312. The digital image signal processing section 312 performs data processes such as off-set correction, gain correction, defective pixel correction, logarithmic conversion on signal intensity, a frequency process, a DR compression process, a gradation process, and sensitivity correction, and outputs digital image data. Details of the digital image signal processing section 312 are omitted.

A sequencer 313 may be configured of a microcomputer, a gate array, etc. The sequencer 313 supplies control signals to the gate selector 306, the charge amplifier 304, the sample and hold circuit section 307, the multiplexer 308, and the A-D converter 311.

Figure 4:
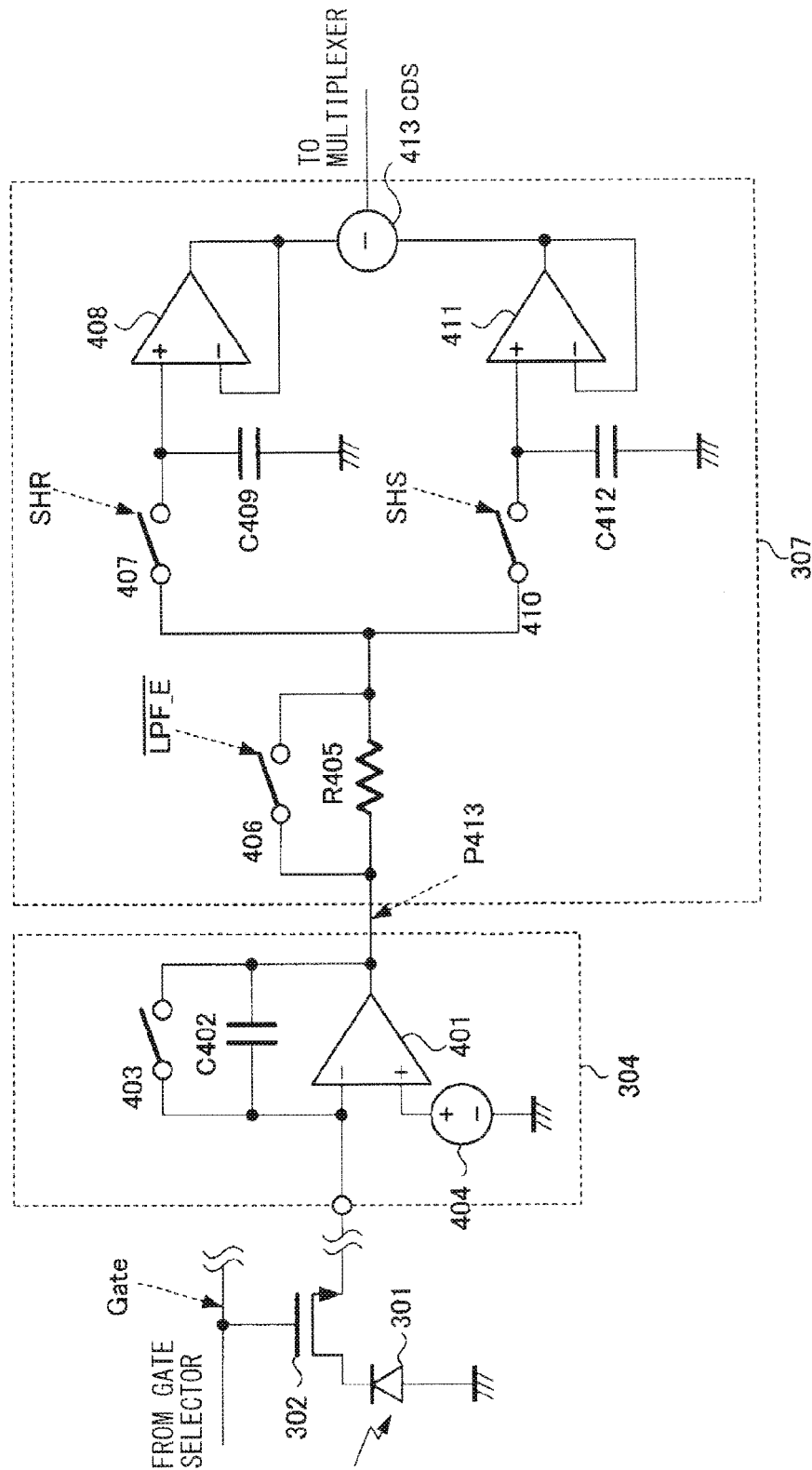
FIG. 4 is a circuit diagram of a charge amplifier and a sample and hold circuit.

FIG. 4 is a circuit diagram of the charge amplifier 304 and the sample and hold circuit section 307.

The X-ray is converted into visible light such as green light by the scintillator 202. When the visible light enters the photodiode 301, electric charge is generated by the photodiode 301 as a result of photoelectric conversion. The electric charge generated by the photodiode 301 is supplied to an inverting input terminal of a first operational amplifier 401 via the pixel transistor 302.

A capacitor C402 is connected between the inverting input terminal and an output terminal of the first operational amplifier 401. The first operational amplifier 401 thus configures the charge amplifier 304. The charge amplifier 304 causes the inputted electric charge to be accumulated in the capacitor C402 and converts the accumulated electric charge into a voltage. It is to be noted that a first switch 403 for discharge is connected to both ends of the capacitor C402, and is controlled by the sequencer 313.

It is to be noted that a constant voltage source 404 is connected to a non-inverting input terminal of the first operational amplifier 401 in order to set a reset level of the pixel transistor 302 and to supply an off-set voltage necessary for a downstream amplifier such as the charge amplifier 304. The voltage of the constant voltage source 404 is commonly provided to all of the first operational amplifiers 401 that are connected to all of the signal lines 303, and equal voltages are applied to all of the signal lines 303 as a result of virtual short of the first operational amplifiers 401.

The output terminal of the first operational amplifier 401 is connected to a resistance R405. A second switch 406 is connected to both ends of the resistance R405, and is controlled by the sequencer 313. The second switch 406 in an OFF state configures a LPF (Low Pass Filter) together with capacitors C409 and C412 described later.

The resistance R405 is connected to a non-inverting input terminal of a second operational amplifier 408 and the capacitor C409 via a third switch 407. Also, the resistance R405 is connected to a non-inverting input terminal of a third operational amplifier 411 and the capacitor C412 via a fourth switch 410 in a similar manner. As can be seen from FIG. 4, the second operational amplifier 408 and the third operational amplifier 411 have completely the same circuit configuration. Description is therefore provided of the second operational amplifier 408 below.

An inverting input terminal of the second operational amplifier 408 is directly connected to an output terminal of the second operational amplifier 408. This configures a voltage follower. The second operational amplifier 408 outputs a voltage of the non-inverting input terminal to the output terminal. When the third switch 407 is turned off, electric charge is held in the capacitor C409, and the operational amplifier therefore configures the sample and hold circuit section 307. Further, when the third switch 407 is turned on and the second switch 406 is turned off, the resistance and the capacitor C409 configure a passive first-order LPF. In other words, the capacitor C409 is a component of the LPF and is also a component of the sample and hold circuit section 307.

As described above, the third operational amplifier 411 also achieves a function similar to the function of the second operational amplifier 408.

The second operational amplifier 408 and the capacitor C409 output a pre-sampling (=reset-sampling) signal of the CDS (Correlated Double Sampling) 413. In other words, the second operational amplifier 408 and the capacitor C409 output a voltage signal at a time when the pixel transistor 302 is turned off. On the other hand, the third operational amplifier 411 and the capacitor C412 output a sampling signal of the CDS 413. In other words, the third operational amplifier 411 and the capacitor C412 output a voltage signal at the time when the pixel transistor 302 is turned on. The CDS 413 outputs a differential of the sampling signal and the reset-sampling signal. The differential signal is amplified in voltage by the downstream amplifier 309 via the multiplexer 308, is then subjected to A-D conversion by the A-D converter 311, and is subjected to a digital image signal process by the digital image signal processing section 312.

[Operation]

Figure 5A:
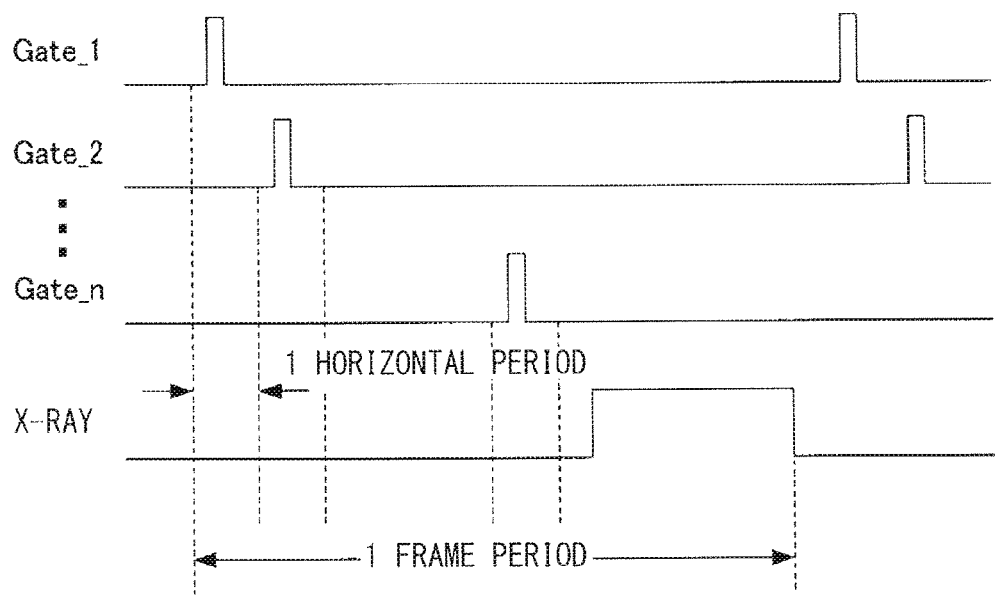
FIG. 5A is a timing chart illustrating control signals outputted by a gate selector and an X-ray produced by an X-ray tube in one frame period.
Figure 5B:
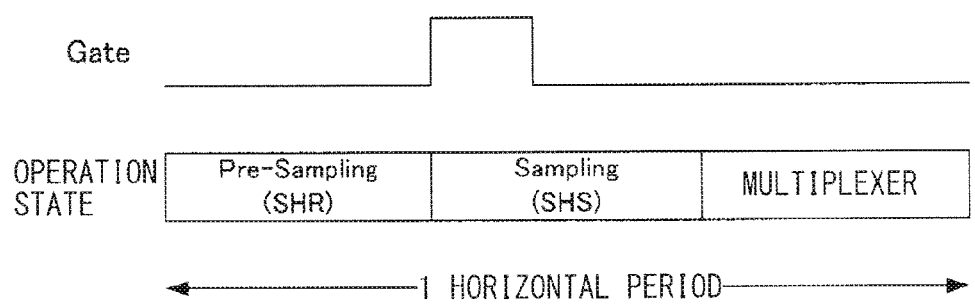
FIG. 5B is a timing chart illustrating a control signal outputted by the gate selector and an operation state of an analog circuit section in one horizontal period.

FIGS. 5A and 5B are a timing chart of the control signals outputted by the gate selector 306 and the X-ray produced by the X-ray tube 102 in one frame period, and a timing chart of the control signals outputted by the gate selector 306 and an operation state of the analog circuit section 203 in one horizontal period.

FIG. 5A is the timing chart of the control signals outputted by the gate selector 306 and the X-ray produced by the X-ray tube 102 in one frame period. The gate selector 306 performs ON-OFF control sequentially on the gate terminals of the pixel transistors 302 for the respective horizontal periods. When the ON-OFF control of all of the gate terminals is completed by the gate selector 306, the sequencer 313 controls the X-ray tube 102 to be turned on. Accordingly, electric charge is generated in the photodiode 301, and the generated electric charge remains to be accumulated in the photodiode 301. The electric charge accumulated in the photodiode 301 moves to the charge amplifier 304 in response to ON control of the pixel transistor 302 performed by the gate selector 306.

FIG. 5B is a timing chart of the control signals outputted by the gate selector 306 and the operation state of the analog circuit section 203 in one horizontal period. The sequencer 313 first controls the sample and hold circuit section 307, and causes a potential of the charge amplifier 304 in a state where the pixel transistor 302 is turned off to be sampled and held by the capacitor C409 and the second operational amplifier 408.

Next, in a state where the gate selector 306 has controlled the pixel transistor 302 to be turned on, the sequencer 313 controls the sample and hold circuit section 307, and causes the potential of the charge amplifier 304 in a state where the pixel transistor 302 is turned on to be sampled and held by the capacitor C412 and the third operational amplifier 411. At this time, the CDS 413 outputs a differential of the output signal of the second operational amplifier 408 and the output signal of the third operational amplifier 411.

Subsequently, the sequencer 313 controls the multiplexer 308 and the A-D converter 311, and thereby causes the output signals of the CDS 413 to be sequentially subjected to A-D conversion.

Figure 6:
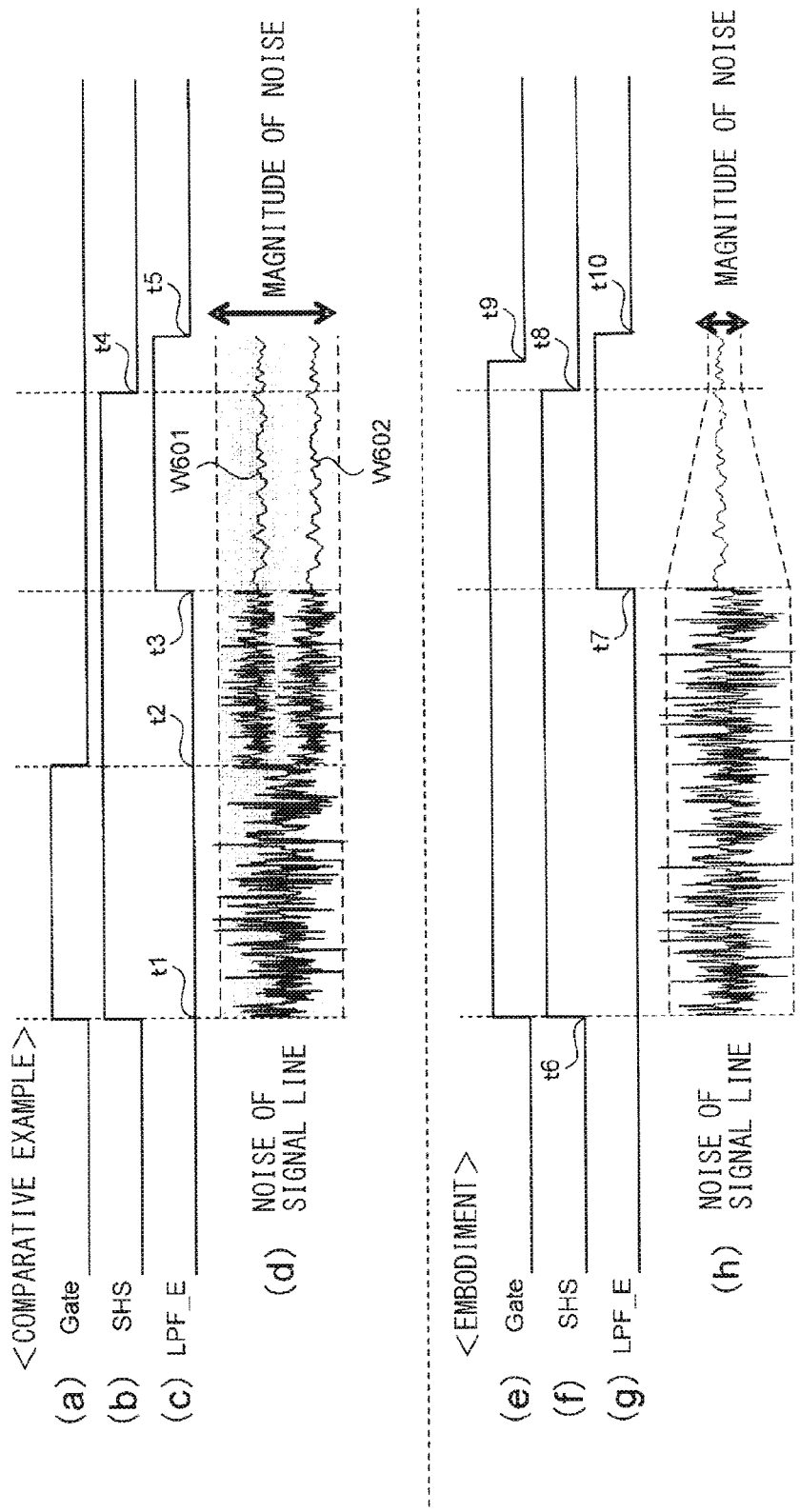
FIG. 6 is a timing chart illustrating control signals outputted by a sequencer and a graph illustrating only a noise component out of an output signal of a third operational amplifier.

FIG. 6 is a timing chart illustrating control signals outputted by the sequencer 313 and the gate selector 306, and a graph illustrating only a noise component out of the output signal of the third operational amplifier 411.

(a) to (d) of FIG. 6 are timing charts for the sequencer 313 and a graph of the noise component according to a comparative example.

(a) illustrates a signal of Gate illustrated in FIG. 4, and represents a control signal to be applied to a gate of the pixel transistor 302. When Gate is at a high potential, the pixel transistor 302 performs an ON operation, and the electric charge in the photodiode 301 thereby flows into the charge amplifier 304.

(b) illustrates a signal of SHS illustrated in FIG. 4, and represents a control signal of the fourth switch 410. When SHS is at a high potential, the capacitor C412 is connected to the resistance R405 or the output terminal of the first operational amplifier 401. In other words, the sample and hold circuit configured of the capacitor C412 and the third operational amplifier 411 performs a sample operation. In contrast, when SHS is at a low potential, the sample and hold circuit performs a hold operation.

(c) illustrates a signal of LPF_E illustrated in FIG. 4, and represents a control signal of the second switch 406. When LPF_E is at a high potential, the second switch 406 is turned off, and both ends of the resistance R405 are not short-circuited. Accordingly, the resistance R405 and the capacitor C412 form the LPF. It is to be noted that this is described by a signal of negation in logic of LPF_E. In other words, ON-OFF control of the second switch 406 is performed by the negation signal of LPF_E.

It is to be noted that, although not illustrated in particular, both of the first switch 403 and the third switch 407 (SHR) are maintained to be turned off in the period in the timing chart illustrated in FIG. 6.

(d) is the graph illustrating only the noise component out of the output signal of the third operational amplifier 411.

From a time t1 to a time t2, Gate is at a high potential. When Gate is at a high potential, the pixel transistor 302 performs an ON operation. Accordingly, the electric charge in the photodiode 301 flows into the charge amplifier 304, and a thermal noise of the pixel transistor 302 itself flows into the charge amplifier 304. A level of the thermal noise is proportional to a resistance value. Although the low-temperature polysilicon TFT used in the present embodiment has a resistance value that is lower than a resistance value of an amorphous silicon TFT, the ON resistance of the pixel transistor 302 still has a resistance value from about 40 kΩ to about 80 kaΩ. A high noise component is therefore outputted from the charge amplifier 304 when Gate is at a high potential. Moreover, what should be noted here is that, when Gate is at a high potential, SHS is also at a high potential, but LPF_E is at a low potential. When LPF_E is at a low potential, the both ends of the resistance R405 are short-circuited, and the LPF configured of the resistance R405 and the capacitor C412 is not formed accordingly. In other words, the noise component is not reduced by the LPF and is outputted as it is to the third operational amplifier 411.

From the time t2 to a time t3, Gate is changed to be at a low potential, but LPF_E remains to be at a low potential. In a state where Gate is changed to be at a low potential and LPF_E remains to be at a low potential, the thermal noise derived from the pixel transistor 302 is eliminated, but a thermal noise of the signal line 303 flows into the charge amplifier 304 and is outputted as it is to the third operational amplifier 411. A resistance value of the wiring is smaller than the resistance value of the pixel transistor 302, and an amplitude of the thermal noise thereof is therefore smaller than an amplitude of the thermal noise of the pixel transistor 302.

From the time t3 to a time t4, SHS is maintained at a high potential, and LPF_E is changed to be at a high potential. In a state where LPF_E is at a high potential, the thermal noise of the wiring is reduced.

From the time t4 to a time t5, LPF_E is maintained at a high potential, and SHS is changed to be at a low potential. When SHS is changed to be at a low potential, the fourth switch 410 is opened, and a voltage between both ends of the capacitor C412 is outputted by the third operational amplifier 411. In other words, the hold operation of the sample and hold circuit is performed. In this period, the final potential of the charge amplifier 304 is outputted to the third operational amplifier 411, and is amplified in voltage by the amplifier 309. Thereafter, the resultant is converted into digital data by the A-D converter 311.

In the above-described operations of the charge amplifier 304 and the sample and hold circuit section 307 including the LPF, when Gate is changed to be from a high potential to a low potential, the charge amplifier 304 holds a potential immediately before the change.

In a period in which Gate is turned on, the electric charge outputted by the photodiode 301 is accumulated in the capacitor C402. In other words, the output signal of the photodiode 301 may be considered to be a small DC component. On the other hand, the thermal noise of the pixel transistor 302 is a white noise and is an alternating current (AC component). When Gate is changed to be from ON to OFF, the potential immediately before the change is held by the capacitor C402 in the charge amplifier 304. Accordingly, the potential of the output signal of the third operational amplifier 411 may be varied largely depending on an amplitude of a thermal noise as illustrated by a waveform W601 and a waveform W602 in (d) of FIG. 6A. In other words, in a driving method according to the comparative example, the thermal noise of the pixel transistor 302 is outputted as it is as a noise component.

(e) to (h) of FIG. 6 are timing charts for the sequencer 313 according to the present embodiment and a graph of the noise component.

As with (a), (e) illustrates the signal of Gate illustrated in FIG. 4, and represents the control signal to be applied to the gate of the pixel transistor 302.

As with (b), (f) illustrates the signal of SHS illustrated in FIG. 4, and represents the control signal of the fourth switch 410.

As with (c), (g) illustrates the signal of LPF_E illustrated in FIG. 4, and represents the control signal of the second switch 406.

As with (d), (h) is the graph illustrating only the noise component out of the signal outputted from the third operational amplifier 411.

From a time t8 (corresponding to the time t4) to a time t9, SHS is changed to be at a low potential while LPF_E is maintained at a high potential. In this period, the final potential of the charge amplifier 304 is outputted to the third operational amplifier 411, and is amplified in voltage by the amplifier 309. Thereafter, the resultant is converted into digital data by the A-D converter 311.

(e) to (h) of FIG. 6 are different from (a) to (d) of FIG. 6 in that the ON period of Gate is extended to a time after SHS if turned off (the time t8) (from the time t6 (corresponding to the time t1) to the time t9). Accordingly, the thermal noise of the pixel transistor 302 and the wiring that is outputted from the charge amplifier 304 is inhibited by the LPF configured of the resistance R405 and the capacitor C412. As a result, it is possible to achieve a detection signal having an extremely-high S/N ratio from which the thermal noise has been removed at the time (the time t8) when SHS is turned off.

It is to be noted that the timing at which LPF_E becomes at a high potential, that is, the time t7 in (e) to (h) of FIG. 6 may be preferably not the same as the time t6. In a case where LPF rises upon turning on of Gate, a time constant of the charge amplifier is increased, which causes long time for reading. LPF is therefore driven to be turned on around a timing at which Gate is turned on to complete the reading and the output voltage of the charge amplifier becomes statically determinate.

Figure 7A:
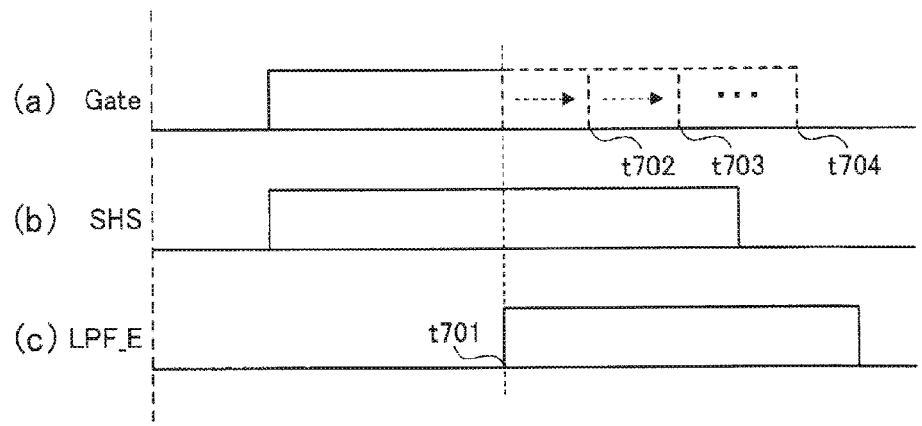
FIG. 7A is a timing chart illustrating that a timing at which Gate is turned off is varied.
Figure 7B:
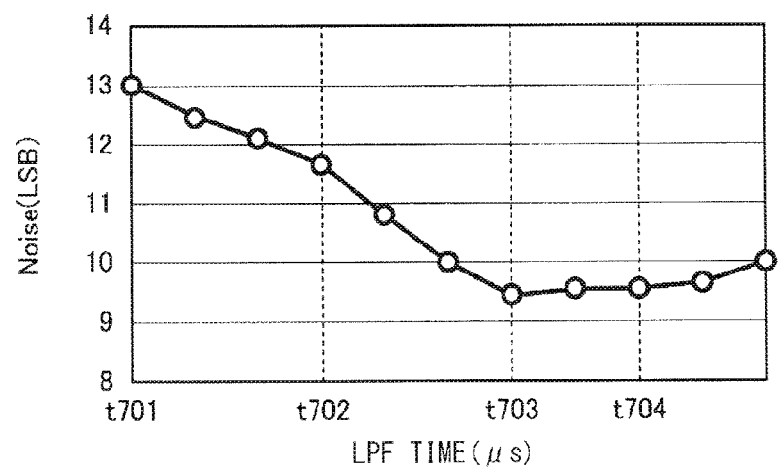
FIG. 7B is a graph illustrating a variation in level of a noise outputted from the third amplifier in the case where the timing at which Gate is turned off is varied.

FIGS. 7A and 7B are a timing chart illustrating that a timing at which Gate is turned off is varied, and a graph illustrating a variation in level of a noise outputted from the third amplifier in the case where the timing at which Gate is turned off is varied.

FIG. 7A is the timing chart illustrating that the timing at which Gate is turned off is varied.

(a) illustrates the signal of Gate illustrated in FIG. 4, and represents the control signal to be applied to the gate of the pixel transistor 302.

(b) illustrates the signal of SHS illustrated in FIG. 4, and represents the control signal of the fourth switch 410.

(c) illustrates the signal of LPF_E illustrated in FIG. 4, and represents the control signal of the second switch 406.

As illustrated in FIG. 7A, the timing at which Gate is turned off is gradually shifted from a time (a time t701: 0 μsec) same as the time at which LPF is turned on to time t702, to time t703, and finally to a time (a time t704) at which 25 μsec has passed since LPF is turned on, and the variation in level of the noise outputted from the third amplifier was measured.

As can be seen from FIG. 7B, LPF functions more effectively as a period from the time at which LPF starts to be ON to the timing at which Gate is turned off is longer.

Figure 8:
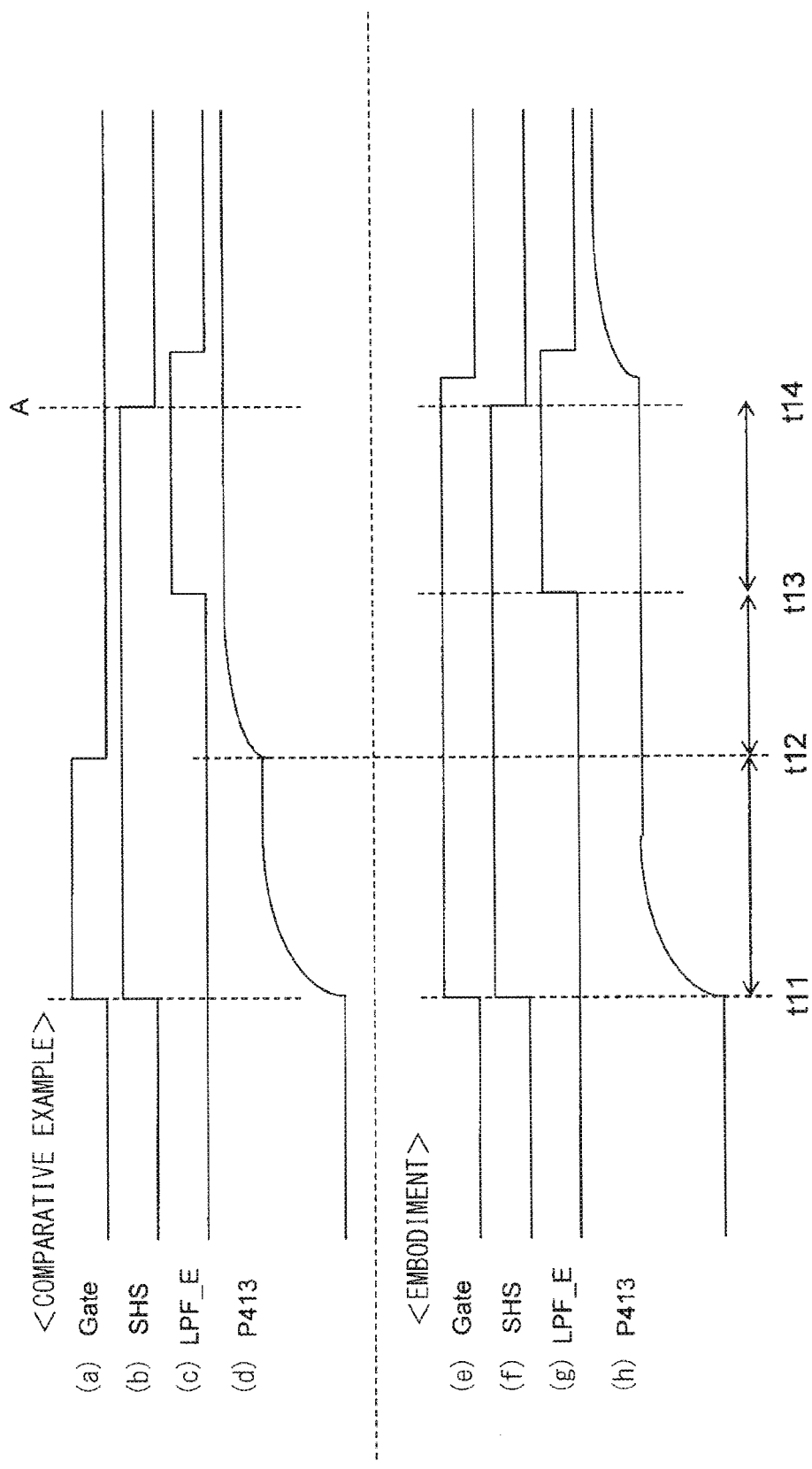
FIG. 8 is a timing chart illustrating the control signals outputted by the sequencer and a graph illustrating a voltage of an output terminal of a first operational amplifier.

FIG. 8 is a timing chart illustrating the control signals outputted by the sequencer 313 and a graph illustrating a voltage of the output terminal of the first operational amplifier 401. It is to be noted that illustration of the noise component is omitted for the sake of easier understanding.

(a) to (d) of FIG. 8 are the timing charts for the sequencer 313 according to the comparative example, and the graph illustrating the voltage of the output terminal of the first operational amplifier 401.

(a) illustrates the signal of Gate illustrated in FIG. 4, and represents the control signal to be applied to the gate of the pixel transistor 302.

(b) illustrates the signal of SHS illustrated in FIG. 4, and represents the control signal of the fourth switch 410.

(c) illustrates the signal of LPF_E illustrated in FIG. 4, and represents the control signal of the second switch 406.

(d) illustrates a signal at a measurement point P413 illustrated in FIG. 4, and illustrates a waveform of the output signal of the charge amplifier 304 from which a noise component is removed.

At a time t12, Gate is changed to be from a high potential to a low potential as illustrated in (a).

MOSFET has a structure that includes respective capacitors between a gate and a drain and between the gate and a source. When a predetermined voltage is applied to the gate, which results in conduction between the drain and the source, one capacitor including the gate, the drain, and the source is configured. When the predetermined voltage that has been applied to the gate is removed to achieve insulation between the drain and the source, one capacitor is divided into two capacitors, that are, a first capacitor including the gate and the drain, and a second capacitor including the gate and the source.

When Gate is turned off, a parasitic capacitance between the gate and the source of the pixel transistor 302 is reduced. Accordingly, part of electric charge accumulated between the gate and the source move into the capacitor C402. This is charge injection that is a phenomenon unique to the sample and hold circuit. As a result, the output voltage of the charge amplifier 304 is increased. Usually, in order to avoid an influence of the charge injection, it is necessary to wait for a predetermined time period until the voltage becomes statically determinate after the pixel transistor 302 is turned off. This is the time period between the time t12 to the time 13 illustrated in FIG. 8.

(e) to (h) of FIG. 8 are timing charts for the sequencer 313 according the present embodiment and a graph illustrating the voltage of the output terminal of the first operational amplifier 401.

(e) illustrates the signal of Gate illustrated in FIG. 4, and represents the control signal to be applied to the gate of the pixel transistor 302.

(f) illustrates the signal of SHS illustrated in FIG. 4, and represents the control signal of the fourth switch 410.

(g) illustrates the signal of LPF_E illustrated in FIG. 4, and represents the control signal of the second switch 406.

(h) illustrates the signal at the measurement point P413 illustrated in FIG. 4, and illustrates the waveform of the output signal of the charge amplifier 304 from which a noise component is removed.

In the present disclosure, Gate remains to be turned on at a time (a time t14) at which SHS is turned off and the sample and hold circuit section 307 is caused to be effective. Accordingly, the charge injection caused by turning off the pixel transistor 302 is less likely to be caused. For this reason, the setting time (from the time t12 to the time t13) provided against the charge injection becomes unnecessary. Unnecessity of the setting time leads to an advantage that higher speed is expected.

The following application examples may be made for the embodiment described above.

(1) The imaging section 104 in the present embodiment employs a sensor having a form in which the scintillator 202 is used, which is called an indirect conversion type. The X-ray is converted into green light by the scintillator 202, and the green light is subjected to photoelectric conversion by the photodiode 301 in the pixel, by which electric charge is read. On the other hand, there may be used a sensor that has a structure in which a film that directly converts the X-ray into electric charge and may be made of amorphous selenium or the like is provided on the pixel instead of the scintillator 202, which is called a direct conversion type. In this case, the pixel has a structure having only a capacitance instead of the photodiode 301.

(2) The timing at which LPF_E rises illustrated in (g) of FIG. 6 may be at the time t6 that is the same as the timing at which Gate in (e) and SHS in (f) rise.

(3) In a case where the low-temperature polysilicon TFT is used, the gate selector 306 may be built in the sensor array 201.

Figure 9:
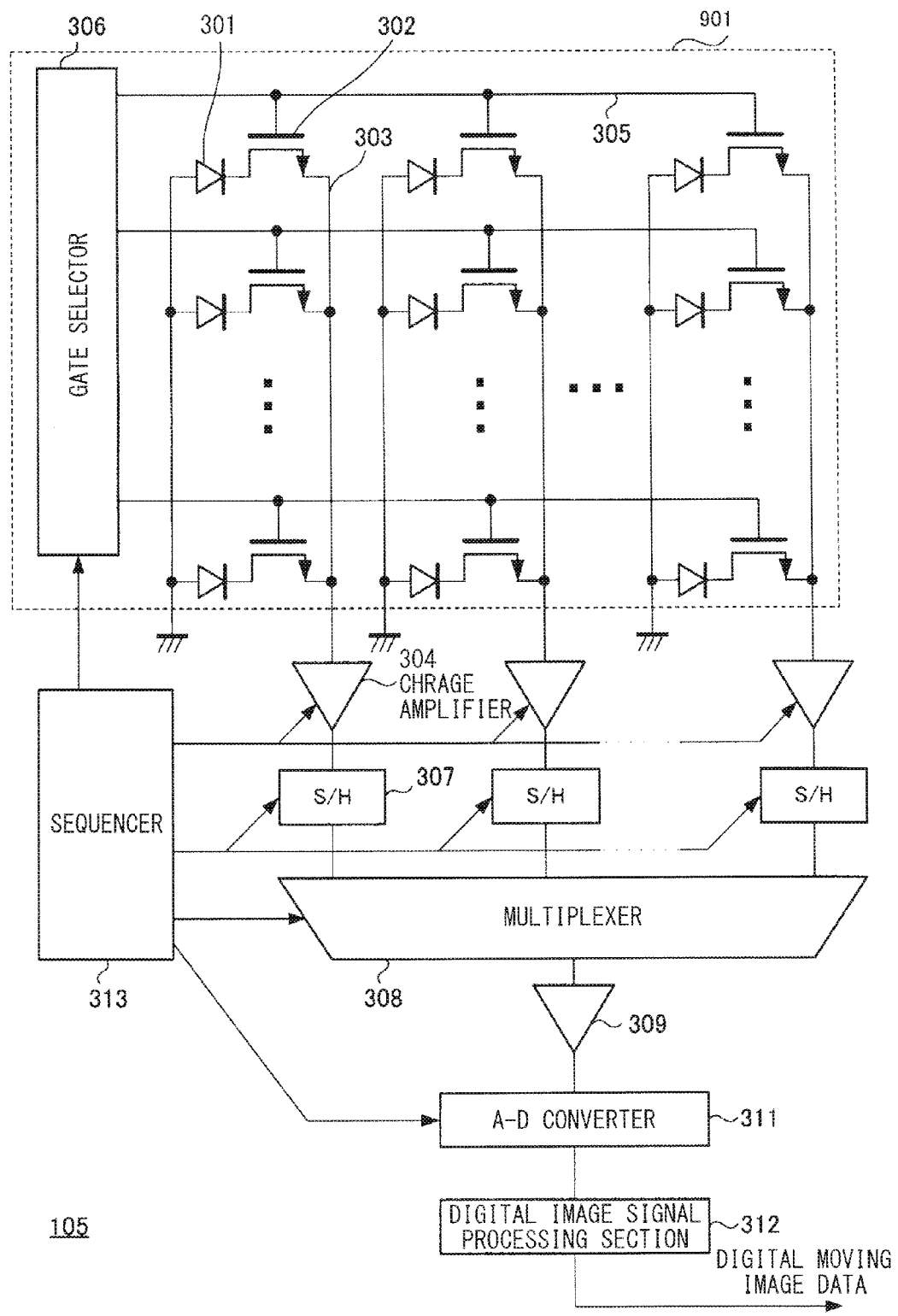
FIG. 9 is a block diagram of a signal processing section that includes a sensor array in another embodiment.

FIG. 9 is a block diagram of the signal processing section 105 that includes a sensor array 201.

FIG. 9 is different from FIG. 3 in that the sensor array 901 also includes the gate selector 306.

(4) In the embodiment described above, the sequencer performs control so as to cause the pixel transistor and the LPF to be effective before the A-D conversion and as to fix sample and hold. In contrast, a control timing for turning off the pixel transistor may be set after the A-D conversion.

(5) The present disclosure may employ the following configurations.

[1]

An imaging unit, including:

a light receiving device configured to receive light and convert the received light into a light detection signal;

a pixel transistor connected to the light receiving device and configured to control connection between the light receiving device and a signal line;

a low-pass filter configured to be applied with respect to the light detection signal;

an A-D converter configured to convert an output signal of the low-pass filter into digital data; and a sequencer configured to, prior to causing the A-D converter to operate to output the digital data, control the pixel transistor to be in an ON state and thereby maintain the light receiving device to be connected to the signal line, in a state in which the low-pass filter is caused to function effectively with respect to the light detection signal.

[2]

The imaging unit according to [1], further including a sample and hold circuit connected between the low-pass filter and the A-D converter, wherein the low-pass filter includes a capacitor, and the sample and hold circuit shares the capacitor with the low-pass filter.

[3]

The imaging unit according to [2], wherein the sequencer controls the pixel transistor to be turned on and causes the low-pass filter to operate, after predetermined time has elapsed thereafter, the sequencer causes the sample and hold circuit to perform a hold operation while maintaining a state in which the pixel transistor is controlled to be in an ON state, and thereafter, the sequencer causes the A-D converter to operate to output the digital data.

[4]

The imaging unit according to [3], further including a charge amplifier configured to convert electric charge outputted from the light receiving device into a voltage and supply the voltage to the low-pass filter, wherein the light receiving device is a photodiode.

[5]

An imaging unit, including:

a light receiving device configured to receive light and convert the received light into a light detection signal;

a pixel transistor connected to the light receiving device and configured to control connection between the light receiving device and a signal line;

a low-pass filter including a capacitor and configured to be applied with respect to the light detection signal;

an A-D converter configured to convert an output signal of the low-pass filter into digital data;

a sample and hold circuit connected between the low-pass filter and the A-D converter, and configured to share the capacitor with the low-pass filter; and a sequencer configured to control the pixel transistor to be in an ON state in a state in which the low-pass filter is caused to function effectively with respect to the light detection signal, after predetermined time has elapsed thereafter, cause the sample and hold circuit to perform a hold operation while maintaining a state in which the pixel transistor is controlled to be in the ON state, cause the A-D converter to operate to output the digital data, and thereafter, control the pixel transistor to be turned off.

[6]

An imaging method, including:

controlling a pixel transistor to be turned on, the pixel transistor being connected to a light receiving device and being configured to control connection between the light receiving device and a signal line, and the light receiving device being configured to receive light and convert the received light into a light detection signal;

causing a low-pass filter to operate with respect to the light detection signal; and after predetermined time has elapsed thereafter, causing a sample and hold circuit to perform a hold operation while maintaining a state in which the pixel transistor is controlled to be in an ON state, the sample and hold circuit being configured to be connected to the low-pass filter.

The radiation imaging unit 101 is disclosed in the present embodiment.

The timing at which the pixel transistor 302 configuring the pixel is turned off is extended to a timing after the time at which the sample and hold circuit section 307 is caused to be effective. Further, at that time, the LPF is caused to function effectively in the period in which the pixel transistor 302 is turned on. Because the thermal noise caused by the pixel transistor 302 and the wiring is removed by the LPF, it is possible to achieve reduction in noise of the imaging section 104 and the signal processing section 105. Accordingly, the S/N ratio is improved, and it is therefore possible to improve image quality of an image shot by the radiation imaging unit 101 and to reduce exposure dose in the radiation imagining unit 101.

Moreover, compared to the driving method according to the comparative example, it is possible to reduce a time for reading the shot image by the signal processing section 105 from the imaging section 104. As a result, it is possible to achieve a higher frame rate compared to the frame rate in the driving method according to the comparative example.

Some embodiment examples of the present disclosure are described above. However, the present disclosure is not limited to the embodiment examples described above, and include other modifications and application examples without departing from the gist of the present disclosure as claimed.

For example, the above embodiment examples are examples that describe the configurations of the unit and the system specifically in detail for the sake of easier understanding, and are not necessarily limited to those having all of the described configurations. Also, it is possible to replace part of the configuration in one example by a configuration in another example. Further, it is also possible to add a configuration in another example to a configuration in one example. Moreover, it is also possible to add another configuration to, remove another configuration from, or substitute another configuration for part of the configuration in each example.

Moreover, part or all of the respective configurations, functions, processing sections, etc. described above may be achieved by hardware. For example, part or all of the respective configurations, functions, processing sections, etc. described above may be designed as an integrated circuit. Moreover, each of the configurations, functions, etc. described above may be achieved by software for interpreting and executing a program for allowing a processer to achieve each of the functions. Information such as a program, a table, a file, and the like for achieving each of the functions may be held in a volatile or non-volatile storage, or in a recording medium. Examples of the volatile or non-volatile storage may include a memory, a hard disk, and an SSD (Solid State Drive). Examples of the recording medium may include an IC card and an optical disk.

Also, the described control lines and information lines described are only those considered to be necessary for the description, and not all of the control lines and the information lines in a product are described. In fact, it may be considered that almost all of the configurations are connected to one another.

This application claims the priority on the basis of Japanese Patent Application JP 2012-222393 filed in Japan Patent Office on Oct. 4, 2012 and Japanese Patent Application JP 2012-254677 filed in Japan Patent Office on Nov. 20, 2012, the entire contents of each which are incorporated herein by reference.

It should be understood by those skilled in the art that various modifications, combinations, sub-combinations, and alterations may occur depending on design requirements and other factors insofar as they are within the scope of the appended claims or the equivalents thereof.

The invention claimed is:

1. An imaging unit, comprising:
a light receiving device configured to receive light and convert the received light into a light detection signal;
a pixel transistor connected to the light receiving device and configured to control connection between the light receiving device and a signal line;
a low-pass filter configured to be applied with respect to the light detection signal;
an A-D converter configured to convert an output signal of the low-pass filter into digital data;
a sample and hold circuit connected between the low-pass filter and the A-D converter, wherein the sample and hold circuit comprises a first circuit and a second circuit; and
a sequencer configured to:
  prior to operation of the A-D converter to output the digital data, control the pixel transistor to be in an ON state and maintain the light receiving device to be connected to the signal line, in a state in which the low-pass filter is caused to function with respect to the light detection signal;
  control the first circuit to output a reset-sampling signal, based on the pixel transistor that is in an OFF state; and
  control the second circuit to output a sampling signal, based on the pixel transistor that is in the ON state.

2. The imaging unit according to claim 1, wherein
the low-pass filter includes a capacitor, and
the sample and hold circuit is configured to share the capacitor with the low-pass filter.

3. The imaging unit according to claim 1, wherein the sequencer is further configured to:
control the pixel transistor to be turned on;
operate the low-pass filter while a state in which the pixel transistor is controlled to be in the ON state is maintained; and
after a determined time from a time when the pixel transistor is turned on has elapsed, cause the sample and hold circuit to hold while the state in which the pixel transistor is controlled to be in the ON state is maintained, and
thereafter, operate the A-D converter to output the digital data.

4. The imaging unit according to claim 3, further comprising
a charge amplifier configured to convert electric charge outputted from the light receiving device into a voltage and supply the voltage to the low-pass filter, wherein the light receiving device is a photodiode.

5. An imaging unit, comprising:
a light receiving device configured to receive light and convert the received light into a light detection signal;
a pixel transistor connected to the light receiving device and configured to control connection between the light receiving device and a signal line;
a low-pass filter that includes a capacitor and is configured to be applied with respect to the light detection signal;
an A-D converter configured to convert an output signal of the low-pass filter into digital data;
a sample and hold circuit connected between the low-pass filter and the A-D converter, and configured to share the capacitor with the low-pass filter, wherein the sample and hold circuit comprises a first circuit and a second circuit; and
a sequencer configured to:
  control the pixel transistor to be in an ON state;
  cause the low-pass filter to function with respect to the light detection signal, while a state in which the pixel transistor is controlled to be in the ON state is maintained;
  after a determined time from a time when the pixel transistor is turned on has elapsed, cause the sample and hold circuit to hold while the state in which the pixel transistor is controlled to be in the ON state is maintained;
  operate the A-D converter to output the digital data;
  thereafter, control the pixel transistor to be turned off;
  control the first circuit to output a reset-sampling signal, based on the pixel transistor that is in an OFF state; and
  control the second circuit to output a sampling signal, based on the pixel transistor that is in the ON state.

6. An imaging method, comprising:
controlling a pixel transistor to be turned on, wherein the pixel transistor is connected to a light receiving device and is configured to control connection between the light receiving device and a signal line, and wherein the light receiving device is configured to receive light and convert the received light into a light detection signal;
operating a low-pass filter with respect to the light detection signal, while a state in which the pixel transistor is controlled to be in an ON state is maintained;
causing an A-D converter to convert an output signal of the low-pass filter into digital data;
after a determined time from the time when the pixel transistor is turned on has elapsed, causing a sample and hold circuit to hold while the state in which the pixel transistor is controlled to be in the ON state is maintained, wherein the sample and hold circuit comprises a first circuit and a second circuit, and is configured to be connected between the low-pass filter and the A-D converter;
controlling the first circuit to output a reset-sampling signal, based on the pixel transistor that is in an OFF state; and
controlling the second circuit to output a sampling signal, based on the pixel transistor that is in the ON state.

7. The imaging unit according to claim 1, wherein the sample and hold circuit is configured to receive an output signal of the low-pass filter as input and the A-D converter is configured to convert output of the sample and hold circuit into the digital data.

* * * * *